Figure 2:
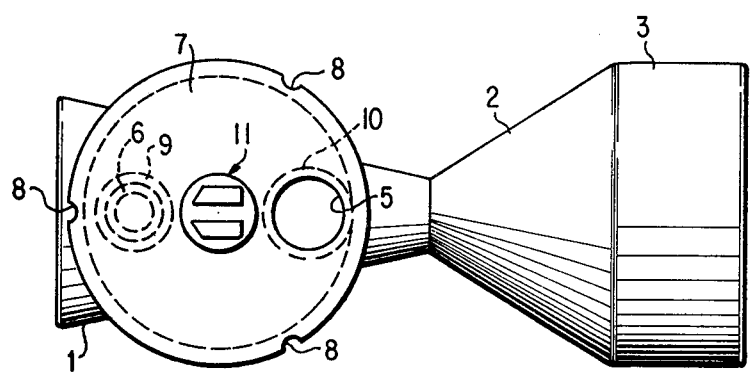
Figure 5:
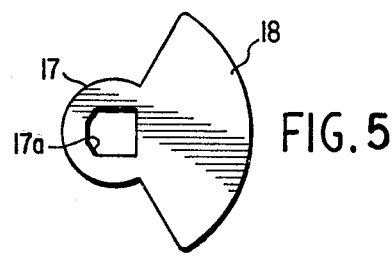

United States Patent [19]

Guenzel et al.

[11] 4,200,099

[45] Apr. 29, 1980

[54] APPARATUS FOR THE INHALATION OF MEDICINAL AGENTS

[75] Inventors: Peter Guenzel; Guenter Rosskamp; Reiner Kolberg; Hans-Juergen Porep, all of Berlin, Fed. Rep. of Germany

[73] Assignee: Schering Aktiengesellschaft, Berlin and Bergkamen, Fed. Rep. of Germany

[21] Appl. No.: 895,671

[22] Filed: Apr. 7, 1978

[30] Foreign Application Priority Data

Apr. 7, 1977 [DE] Fed. Rep. of Germany ....... 2716323

[51] Int. Cl.² ............................................. A61M 15/00
[52] U.S. Cl. ..................................... 128/266; 222/362; 222/636; 406/130
[58] Field of Search ......................... 128/266, 206, 208; 222/362, 370, 193; 302/57, 49

[56] References Cited

U.S. PATENT DOCUMENTS 3,991,908  11/1976  Thomas et al. .................. 222/370 X

FOREIGN PATENT DOCUMENTS 2529522  1/1977  Fed. Rep. of Germany .

Primary Examiner—Henry J. Recla
Attorney, Agent, or Firm—Millen & White

[57] ABSTRACT

Apparatus for inhalation of medicinal agents as an aerosol effluent from the apparatus which includes a housing with a venturi-shaped interior configuration providing a venturi constriction between an air inlet chamber and a aerosol exhaust chamber including a dispenser zone; and with an arrangement for mounting a medicament container on the housing and including a connector member mounted on the housing and apertured for communication therewith, and a metering disk to carry the medicament container and rotatably mounted on the connector member by a related mounting and locking pin arrangement permitting rotation of the metering disk for dosage dispensing while separating a selected dosage chamber from the medicament container during dispensing; the mounting and locking pin arrangement permitting ready separation of the parts for cleaning of residual medicament and re-assembly for further dispensing as with a different medicament.

6 Claims, 6 Drawing Figures

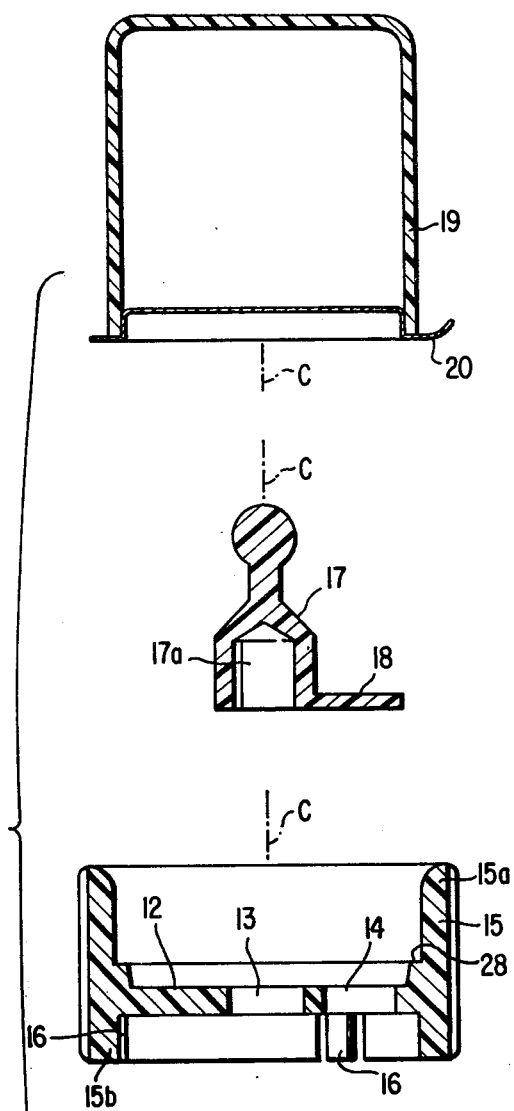
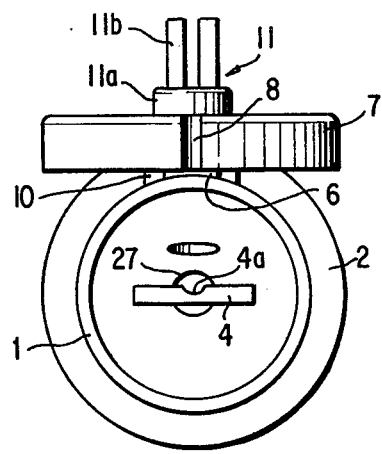
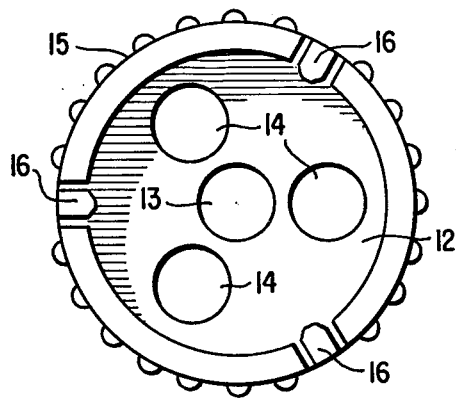
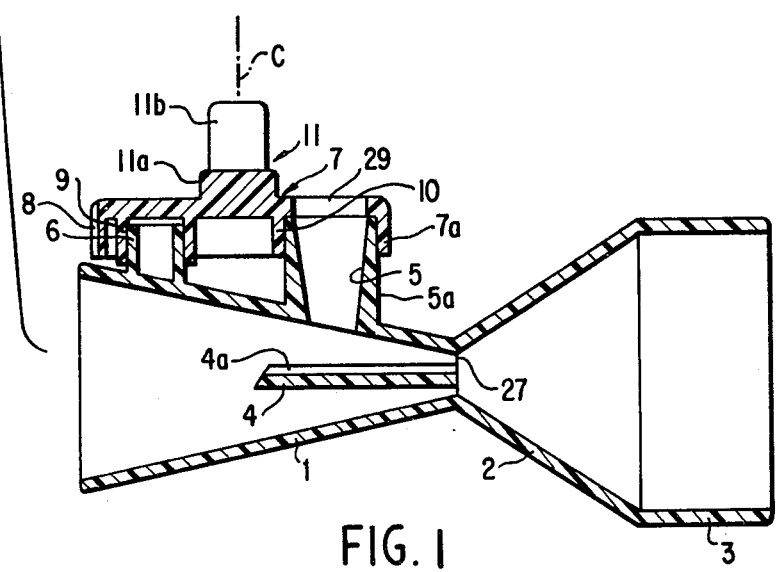
FIG. 1
FIG. 3
FIG. 4

APPARATUS FOR THE INHALATION OF MEDICINAL AGENTS

BACKGROUND OF THE INVENTION

The administration of medicinal agents by inhalation for treatment of diseases of the respiratory tract is known. Such administration has often been accomplished with the aid of compressed air, a propellant gas or the like forming an aerosol effluent to be inhaled. Accurate dosing is difficult and a large proportion of the medicinal agent may go beyond the respiratory tract with undesired side effects. Administration of medicinal agents as an aerosol has also been accomplished by patient inhalation with movable elements serving to atomize the medicaments. In many of these prior devices, the various parts are formed by step by step mechanical manufacture, thus rendering the same relatively expensive to produce. In U.S. Pat. No. 4,046,146, inhalation by the patient serves to create an aerosol effluent without moving parts and with accuracy as to each dosage by employing a metering arrangement for dispensing an accurate dosage to a housing with an internal venturi configuration through the constriction of which air is drawn by inhalation and medicinal agents are delivered in the vicinity of the constriction for passage to a dispenser zone and to an aerosol exhaust section formed as a mouthpiece or nasal appliance from which the effluent is inhaled by the patient.

SUMMARY OF THE INVENTION

The present invention is concurred with inhaling of pulverulent medicinal agents, powdered or micronized, according to certain forms of devices shown in the aforesaid U.S. Pat. No. 4,046,146. Thus, the apparatus includes a support housing with an interior venturi-shaped configuration and a dispensing opening for delivery of medicinal agents in the vicinity of the venturi constriction to be picked up by the induced airstream for passage to the diffuser and aerosol exhaust sections. A connector member is mounted on the housing with a transfer opening aligned with the dispensing opening and a metering disk is mounted on the connector member by a combined mounting and locking pin arrangement permitting selective rotation of the metering disk to dispense dosages through the aforesaid aligned openings from a medicament container carried by the metering disk.

An object of this invention is to provide an apparatus substantially of the above type wherein the parts may be readily separated for cleaning and readily re-assembled.

Another object of this invention is to provide an apparatus substantially of the above type with mounting and locking pin means constructed and arranged for mounting an apertured metering disk for permissive rotation bringing an aperture into dose dispensing position while closing the aperture in the dose dispensing position against the medicament supply in the container.

A further object of the invention is to provide a mounting and locking pin arrangement substantially of the above type wherein the mounting and locking components may be readily separated for the parts to be cleaned without clogging.

The invention still further aims to provide an apparatus substantially of the above type wherein the several parts lend themselves to production by relatively inexpensive injection molding techniques from synthetic resins.

The above and other objects of the invention will in part be obvious and will be hereinafter more fully pointed out in the detail description of the drawings in which, FIG. 1 is a longitudinal section through a drug container, a locking component of the mounting pin, a metering disk, and a housing having the shape of a venturi tube with an inhaling aid and a connecting member attached thereto and showing the pin mounting component;

FIG. 2 is a top plan view of FIG. 1;

FIG. 3 is a front elevation of FIG. 2;

FIG. 4 is a bottom plan view of the metering disk;

FIG. 5 is a bottom plan view of the locking component of the mounting pin; and FIG. 6 is a longitudinal section through the venturi-shaped housing with a nasal type inhaling aid attached thereto.

The housing, having the shape of a venturi tube, comprises two joined chambers 1 as the air inlet chamber and 2 as the diffuser chamber each having the shape of a hollow truncated cone meeting at the venturi constriction 27. The inhaling aid 3, having the shape of a hollow cylinder as a mouthpiece, is arranged at the rear chamber 2. A wedge-shaped catch plate 4 is arranged in the interior of the forward chamber 1, delivering in the vicinity of constriction 27, and having a longitudinal groovelike indentation 4*a* and being flush with the sidewalls of the chamber 1. At the top side of the forward chamber 1, a funnel-shaped aperture 5 is arranged which serves for emptying purposes and the external surface provides a tubular holder 5*a*. A further tubular holder 6 is attached to the forward chamber 1.

For reasons of manufacturing technique, the connecting member 7 is produced separately and connected subsequently by pressure fit to the venturi-tube housing. The connecting member 7 is of a disk shape and has a rim 7*a* along the underside in which three spaced groove-like indentations 8 are disposed. On the underside, the connecting member has two tubular holders 9 and 10 which are pressed onto the external surface 5*a* of the aperture 5 serving for emptying purposes and onto the tubular holder 6 of the venturi-tube housing. The connecting member has an opening 29 above the rearward holder aligned with aperture 5. In the center of the topside of the connecting member is a mounting pin 11. The latter is cylindrical in its lower portion 11*a*, while it is square in its upper portion 11*b*. The square 11*b* is bifurcated by a cutout, and its front edge is beveled.

The metering disk 12 has a central bore 13 which is somewhat larger than the cylindrical portion of the mounting pin 11, three metering chambers 14 arranged centrally symmetrically to one another, and a rim 15 including upper and lower rim portions 15*a*, 15*b*. The rim is fashioned so that the metering disk can be laid flush on the connecting member 7 and so that the drug container can be placed on the metering disk resting on ledge 28. The lower edge 15*b* of the rim has cutouts in which are disposed three detent pins 16 which after attachment of the metering disk engage into the groove-like indentations 8 of the connecting member 7.

The locking or cap portion 17 includes a segment-shaped cover flange 18 on its side, and has a cavity 17*a* complementally shaped to snug the pin part 11b so that it can be placed flush on that part of the holding pin 11 and held against rotation. The drug container 19 has the shape of a cup and is sealed with a foil 20 which is removed before the drug container is inserted in the inhaling apparatus resting on the ledge 28 of the metering disk 15.

In assembled position, the parts of FIGS. 1 are nested together as indicated by the broken center lines C. Thus, when assembled, the flange portion 15a of the metering disk will engage over the periphery of the connector disk 7 with the detents 16 engaging in corresponding recesses 8 and the round pin portion 11a will fit within the circular opening 13 in the metering device which is thus permitted to rotate according to the indexing of 8 and 16 to align a selected one of the metering chambers 14 with opening 29 in the connector disk 15 and the dispensing opening 5 in the housing. The cap portion 17 of the pin is fitted over the pin with the recess or cavity 17a frictionally engaging the bifurcated end 11b and held against rotation with the cover flange overlying the selected opening 14 shifted therebeneath for dispensing and thus sealing off the remainder of the contents of the container 19 against discharge.

In operation of the assembly, the detents and recesses are oriented to selectively position one of the metering chambers with included medicament over the transfer opening 29 and the dispensing opening 5 for delivery of the medicament dose to the plate 4 from which the induced air stream from inhalation through the mouthpiece will be directed through the venturi constriction 27 to the diffuser zone 2 and thence into the respiratory tract of the patient. The metering disk is permitted to rotate around the pin portion 11a but the cover flange 18 of the locking or cup portion 17 remains fixed by reason of the interengaged out-of-round recess 17a and the squared and bifurcated portion 11b of the mounting pin. The assembly is one which may be conveniently taken apart for cleaning by removal of the cap portion 17 and then the metering and connector disks. When so dis-assembled for cleaning, any drug dust remaining from a prior dispensing will be removed and the re-assembled parts can be used for dispensing another medicament, thus greatly prolonging useful life of the assembly.

Figure 6:
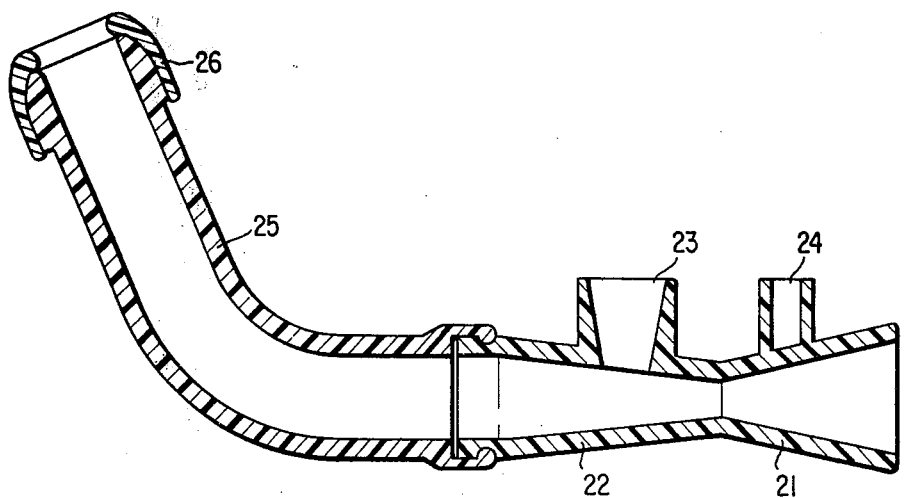

In FIG. 6, the housing includes the two joined chambers 21 serving as the inlet chamber and 22 serving as the diffuser zone, each having the shape of a hollow truncated cone, with the funnel-shaped aperture 23 extending upwardly from the diffuser zone and serving for emptying purposes upstream of the constriction, and with the tubular holder 24 extending upwardly from the inlet chamber. The tubular inhaling aid 25 can be attached to the venturi-like housing; this inhaling aid for nasal inhalation is bent upwardly and carriers a removable, conical cap 26. The remaining components of this apparatus are substantially the same as in the inhaling device previously described and operates in similar manner, after mounting on the housing by the holders.

What is claimed is:

1. In an apparatus for the inhalation of medicinal agents as an aerosol effluent from the apparatus which includes a housing with a venturi tube-shaped interior configuration and with a dispensing aperture opening into the housing in the vicinity of the venturi constriction which is between an air inlet chamber and an exhaust chamber from which the aerosol effluent is inhaled; the provision of a metering mechanism comprising a connector member detachably mounted in fixed position on said housing and having a transfer aperture aligned with the dispensing aperture in said housing; a metering disk rotably mounted on said connector member and including means adapted to support a medicament container and having a central opening and at least one metering chamber therethrough radially outwardly of the said central opening and alignable with said transfer aperture; and composite mounting means detachably connecting said metering disk to said connector member for permissive rotation of the metering disk to selectively align a metering chamber with the aligned transfer and dispensing apertures for discharging a metered dose of medicament into the venturi tube-shaped interior of the housing and for closing the metering chamber against access of additional medicament thereto from the container, said composite mounting means including a pin component extending from said connector member and having an upper portion and a lower circular portion, said central opening being rotatably mounted on said circular portion thereby permitting the rotation of the metering disk and a locking cap component in removable non-rotating engagement with the upper portion of the pin component for securing said metering disk to said connector member, said locking cap component including a lateral extension covering said metering chamber when aligned with said transfer aperture.

2. Apparatus according to claim 1, wherein the upper portion of the pin component is out-of-round, and wherein the locking cap component is provided with an internal out-ofround recess in complement to the upper portion of the pin component and assembled therewith in non-rotative rotation.

3. Apparatus according to claim 2, wherein the out-of-round upper portion is bifurcated to frictionally fit within the locking component.

4. Apparatus according to claim 1, wherein the housing comprises two chambers each having the shape of a hollow truncated cone, connected together at their apices to form the venturi constriction.

5. Apparatus according to claim 1, wherein there is provided an inhaling aid in the shape of a hollow cylinder at the end of the exhaust chamber.

6. Apparatus according to claim 1, wherein there is provided a tubular inhaling aid which is bent in the upward direction from the end of the exhaust chamber.

* * * * *